(12) United States Patent
Takeuchi et al.

(10) Patent No.: US 7,763,625 B2
(45) Date of Patent: Jul. 27, 2010

(54) AGENTS FOR TREATING MIGRAINE

(75) Inventors: Megumi Takeuchi, Port Jefferson, NY (US); Makoto Takayama, Sunto-gun (JP); Shiro Shirakura, Mishima (JP); Hiroshi Kase, Koganei (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 804 days.

(21) Appl. No.: 10/587,264

(22) PCT Filed: Jan. 28, 2005

(86) PCT No.: PCT/JP2005/001634
§ 371 (c)(1),
(2), (4) Date: Sep. 11, 2006

(87) PCT Pub. No.: WO2005/072739
PCT Pub. Date: Aug. 11, 2005

(65) Prior Publication Data
US 2007/0161663 A1 Jul. 12, 2007

(30) Foreign Application Priority Data
Jan. 28, 2004 (JP) .................... 2004-019496

(51) Int. Cl.
A01N 43/90 (2006.01)
A61K 31/52 (2006.01)
A61K 31/522 (2006.01)

(52) U.S. Cl. ................. 514/263.2; 514/263.34

(58) Field of Classification Search ............ 514/263.2, 514/263.34
See application file for complete search history.

(56) References Cited

U.S. PATENT DOCUMENTS

| | | | | |
|---|---|---|---|---|
| 3,641,010 A | * | 2/1972 | Schweiss et al. | 544/267 |
| 4,599,338 A | | 7/1986 | Regnier et al. | 514/265 |
| 5,484,920 A | | 1/1996 | Suzuki et al. | 544/268 |
| 5,543,415 A | | 8/1996 | Suzuki et al. | 514/263 |
| 5,670,498 A | | 9/1997 | Suzuki et al. | 514/212 |
| 5,756,735 A | | 5/1998 | Suzuki et al. | 544/267 |
| 6,187,780 B1 | | 2/2001 | Blech et al. | 514/263 |
| 6,245,900 B1 | | 6/2001 | Yamasaki et al. | 530/402 |
| 6,579,868 B1 | | 6/2003 | Asano et al. | 514/211.08 |
| 6,727,259 B2 | | 4/2004 | Shimada et al. | 514/263.34 |

FOREIGN PATENT DOCUMENTS

| | | |
|---|---|---|
| EP | 0 565 377 | 8/1993 |
| WO | WO 97/01551 | 1/1997 |

OTHER PUBLICATIONS

Chen et. al., The Journal of Neuroscience, 2001, Society for Neuroscience, vol. 21, pp. RC14391-6).*
Strong, Journal of Pharmacy & Pharmacology, 1997, Royal Pharmaceutical Society of Great Britain, vol. 49, p. 1260.*
Villalón, et al., "Effects of S9977 and dihydroergotamine in an animal experimental model for migraine", *Pharmacological Research* (1992), vol. 25, No. 2, pp. 125-137.
Guieu, et al., "Adenosine and migraine", *Can. J. Neurol. Sci.* (1998), vol. 25, No. 1, pp. 55-58.
Ngai, et al., "Receptor subtypes mediating adenosine-induced dilation of cerebral arterioles", *Am J Physiol Heart Circ Physiol* (2001), vol. 280, p. H2329-H2335.
Honey, et al., "Study of an adenosine A1 receptor agonist on trigeminally evoked dural blood vessel dilation in the anaesthetized rat", *Cephalalgia* (2002), vol. 22, p. 260-264.
Erickson, et al, "1,3,8-Trisubstituted Xanthines. Effects of substitution pattern upon adenosine receptor $A_1/A_2$ affinity", *J. Med. Chem.*, (1991), vol. 34, p. 1431-1435.
Jacobson, et al., "Structure-activity relationships of 8-styrylxanthines as $A_2$-selective adenosine antagonists", *J. Med. Chem.* (1993), vol. 36, p. 1333-1342.
Fredholm, et al., Actions of Caffeine in the Brain with Special Reference to Factors that Contribute to Its Widespread Use, Pharmacological Reviews, vol. 51, No. 1 (1999) 83-133.
Ishiyaku Shuppan's Medical Dictionary 2nd Edition (1998) which reports in Japanese "the smooth muscle relaxation by caffeine is explained by increased cAMP level in the tissue caused by the inhibition of PDE activities").
MeSH Database of PubMed (NCBI) (http://www.ncbi.nlm.nih.gov/mesh, 1979.

* cited by examiner

*Primary Examiner*—Sreeni Padmanabhan
*Assistant Examiner*—Sarah Pihonak
(74) *Attorney, Agent, or Firm*—Fitzpatrick, Cella, Harper & Scinto

(57) ABSTRACT

A method for treating migraine comprising administering, as an active ingredient, a xanthine derivative represented by the following formula or a pharmaceutically acceptable salt thereof.

1 Claim, 1 Drawing Sheet

AGENTS FOR TREATING MIGRAINE

TECHNICAL FIELD

The present invention relates to agents for treating migraine comprising, as an active ingredient, a xanthine derivative or a pharmaceutically acceptable salt thereof.

BACKGROUND ART

Migraine is a paroxysm of headache lasting 4 to 72 hours, which is accompanied by nausea, vomiting, extreme sensitivity to light and sound, and the like [Merck Manual, 17th Edition, Section 168; Therapeutic Guideline of Japanese Society of Neurology (Societal Neurologica Japonica); International Classification of Headache Disorders-II: ICHD-II, 2004]. As one of pathophysiology of migraine and the underlying mechanisms, vasodilation of extra- and/or intra-cranial blood vessels including superficial temporal artery has been proposed [Arch. Neurol. Psychiatr., vol. 39, p. 737-763 (1938); Cephalalgia, vol. 1, p. 143-147 (1981); Naika (Internal Medicine), vol. 81, p. 601-609 (1998); Naika, vol. 81, p. 639 (1998)]. It has also been known that the hydrophilic agonists of serotonin receptor 5-HT$_1$ (5-hydroxytryptamine 1) such as ergot alkaloid and sumatriptan, which poorly cross the blood brain barrier, are effective for the treatment of migraine since they can contract the dilated cranial blood vessels via the serotonin receptor 5-HT$_1$ of cerebral artery [Ann. N.Y. Acad. Sci., vol. 600, p. 587-600 (1990); Neurology, vol. 43, p. S43-S47 (1993)].

Thus, it has been assumed that migraine could be treated by suppressing vasodilation of the extra- and/or intra-cranial blood vessels.

On the other hand, it has also been reported that the adenosine concentrations in the plasma of patients suffering from migraine are increased at an average of 68% at one hour after the migraine attack compared with those in crisis-free periods, that activation A$_2$ receptors by adenosine causes a dose-dependent serotonin uptake by platelets and consequently the vasodilation is induced by rapid reduction of serotonine [Can. J. Neurol. Sci., vol. 2, p. 55-58 (1998)], and that intravenous injection of the adenosine potentiator to patients suffering from migraine induces the migraine attack [Med. J. Aust., vol. 162, p. 389-390 (1995)]. In addition, it has been known that adenosine has a potent vasodilating action and that an adenosine A$_{2A}$ receptor and an adenosine A$_{2B}$ receptor are involved in the vasodilation during the migraine attack and in the vasodilation induced by adenosine [Am. J. Physiol. Heart Circ. Physiol., vol. 280, p. 2329-2335 (2001)]. In view of these facts, it has been considered that migraine could be treated by suppression of vasodilation induced by adenosine.

It has also been known that caffeine has an adenosine antagonistic action with low specificity and acts to relieve migraine headache, though caffeine induces drug dependence as a side effect and causes a caffeine-withdrawal headache [ref.: Pain, 1991; vol. 44, p. 151-155; and Drugs, 1998, vol. 49, p. 37-50].

Pyrazole derivatives with adenosine antagonistic activity (WO97/01551), adenosine A$_1$ receptor agonists such as GR79236 (ref: Cephalalgia, 2002, vol. 22, p. 260-264), and the like are known to have a therapeutic effect for migraine.

On the other hand, many of xanthine derivatives including the compounds represented by the formula (I) as mentioned below have been known to have, for example, adenosine A$_2$ receptor antagonistic action, anti-Parkinsonian action, central nerve exciting action, suppressive action on neurodegeneration, antidepressive action, anti-asthma action, suppressive action for bone resorption, hypoglycemic action, suppressive action for thrombocytosis, and the like [Japanese Published Examined Patent Application No. 26516/1972, Japanese Published Unexamined Patent Application No. 211856/1994, Japanese Published Unexamined Patent Application No. 239862/1994, Japanese Published Unexamined Patent Application No. 16559/1994, WO92/06976, WO94/01114, WO95/23165, WO99/12546, WO99/35147; J. Med. Chem., vol. 34, p. 1431 (1991); J. Med. Chem., vol. 36, p. 1333 (1993)].

DISCLOSURE OF THE INVENTION

An object of the present invention is to provide agents for treating migraine comprising, as an active ingredient, for example, a xanthine derivative or a pharmaceutically acceptable salt thereof, and the like.

The present invention relates to the following (1) to (7).

(1) An agent for treating migraine comprising, as an active ingredient, a xanthine derivative represented by formula (I):

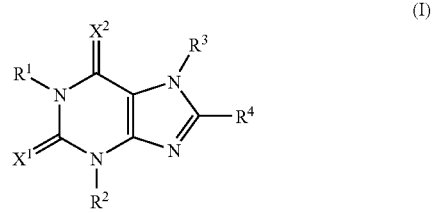

[wherein R$^1$, R$^2$ and R$^3$ are the same or different, and represent a hydrogen atom, lower alkyl, lower alkenyl or lower alkynyl;

R$^4$ represents cycloalkyl, —(CH$_2$)$_n$—R$^5$ (wherein R$^5$ represents substituted or unsubstituted aryl, or substituted or a unsubstituted heterocyclic group; and n represents an integer of 0 to 4) or a group represented by formula (II):

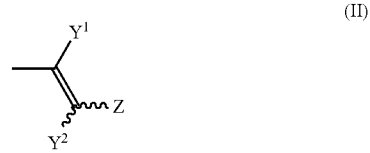

(wherein Y$^1$ and Y$^2$ are the same or different, and represent a hydrogen atom, halogen or lower alkyl; and Z represents substituted or unsubstituted aryl or a substituted or unsubstituted heterocyclic group);

X$^1$ and X$^2$ are the same or different, and represent an oxygen atom or a sulfur atom]

or a pharmaceutically acceptable salt thereof.

(2) The agent for treating migraine according to the above (1), wherein X$^1$ and X$^2$ are both an oxygen atoms.

(3) The agent for treating migraine according to the above (1) or (2), wherein R$^4$ is a group represented by formula (II):

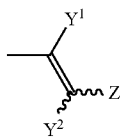

(wherein $Y^1$, $Y^2$ and Z each have the same meanings as defined above).

(4) The agent for treating migraine according to the above (3), wherein $Y^1$ and $Y^2$ are both hydrogen atoms.

(5) The agent for treating migraine according to the above (3) or (4), wherein Z is substituted or unsubstituted aryl or a group represented by formula (III):

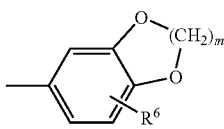

(wherein $R^6$ represents a hydrogen atom, hydroxy, lower alkyl, lower alkoxy, halogen, nitro or amino; and m represents an integer of 1 to 3).

(6) A method for treating migraine which comprises administering an effective amount of a xanthine derivative represented by formula (I):

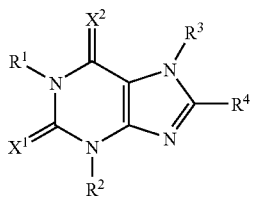

(wherein $R^1$, $R^2$, $R^3$, $R^4$, $X^1$ and $X^2$ each have the same meanings as defined above)

or a pharmaceutically acceptable salt thereof.

(7) Use of a xanthine derivative represented by formula (I):

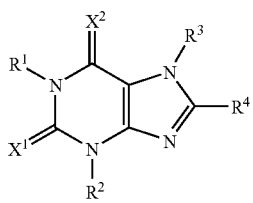

(wherein $R^1$, $R^2$, $R_3$, $R^4$, $X^1$ and $X^2$ each have the same meanings as defined above)

or a pharmaceutically acceptable salt thereof for the manufacture of an agent for treating migraine.

In the definition of each group in formula (I):

Examples of the lower alkyl and the lower alkyl moiety of the lower alkoxy include straight-chain or branched alkyl having 1 to 6 carbons, such as methyl, ethyl, propyl, isopropyl, butyl, isobutyl, sec-butyl, tert-butyl, pentyl, neopentyl and hexyl.

Examples of the lower alkenyl include straight-chain or branched alkenyl having 2 to 6 carbons, such as vinyl, allyl, methacryl, crotyl, 3-butenyl, 2-pentenyl, 4-pentenyl, 2-hexenyl and 5-hexenyl.

Examples of the lower alkynyl include straight-chain or branched alkynyl having 2 to 6 carbons, such as ethynyl, propargyl, 2-butynyl, 3-butynyl, 2-pentynyl, 4-pentynyl, 2-hexynyl, 5-hexynyl and 4-methyl-2-pentynyl.

Examples of the cycloalkyl include cycloalkyl having 3 to 8 carbons, such as cyclopropyl, cyclobutyl, cyclopentyl, cyclohexyl, cycloheptyl and cyclooctyl.

The halogen means an atom of fluorine, chlorine, bromine and iodine.

Examples of the aryl include those having 6 to 14 carbons, such as phenyl, naphthyl and anthryl.

Examples of the heterocyclic group include 5- or 6-membered monocyclic heterocyclic groups containing at least one atom selected from a nitrogen atom, an oxygen atom and a sulfur atom; bicyclic or tricyclic condenced-ring heterocyclic groups containing at least one atom selected from a nitrogen atom, an oxygen atom and a sulfur atom in which 3 to 8-membered rings are condensed and the like. Specific examples thereof include furyl, thienyl, pyrrolyl, pyranyl, thiopyranyl, pyridyl, pyrimidinyl, triazinyl, purinyl, pyrazinyl, pyridazinyl, benzimidazolyl, 2-oxobenzoimidazolyl, benzotriazolyl, benzofuryl, benzothienyl, benzoxazolyl, benzothiazolyl, 1,3-benzodioxolyl, 1,4-benzodioxanyl, 3,4-dihydro-2H-1,5-benzodioxepinyl, indazolyl, indolyl, isoindolyl, quinolyl, isoquinolyl, phthalazinyl, naphthyridinyl, quinoxalinyl, pyrazolyl, quinazolinyl, cinnolinyl, triazolyl, tetrazolyl, imidazolyl, oxazolyl, isoxazolyl, thiazolyl, isothiazolyl, dihydroisoquinolyl, tetrahydroquinolyl, dihydrobenzopyranyl and the like.

Examples of the substituents in the substituted aryl and the substituted heterocyclic group may be the same or different in number of 1 to 3. Specific examples thereof include lower alkyl, lower alkenyl, lower alkynyl, hydroxy, substituted or unsubstituted lower alkoxy, halogen, nitro, amino, lower alkylamino, di-lower alkylamino, trifluoromethyl, trifluoromethoxy, aralkyl, aralkyloxy, aryl, aryloxy, lower alkanoyl, lower alkanoyloxy, aroyl, aroyloxy, arylalkanoyloxy, carboxy, lower alkoxycarbonyl, lower alkylcarbamoyl, di-lower alkylcarbamoyl, sulfo, lower alkoxysulfonyl, lower alkylsulfamoyl, di-lower alkylsulfamoyl and the like.

The lower alkyl moiety of the above-described lower alkyl, lower alkoxy, lower alkylamino, di-lower alkylamino, lower alkanoyl, lower alkanoyloxy, lower alkoxycarbonyl, lower alkylcarbamoyl, di-lower alkylcarbamoyl, lower alkoxysulfonyl, lower alkylsulfamoyl and di-lower alkylsulfamoyl has the same meaning as the above-described lower alkyl. The halogen, the lower alkenyl and the lower alkynyl have the same meanings as described above, respectively. Two lower alkyl moieties of the di-lower alkylamino, the di-lower alkylcarbamoyl and the di-lower alkylsulfamoyl may be the same or different. The aryl moiety of the aryl and the aryloxy is the same as the above-described aryl, and examples of the aralkyl moiety of the aralkyl and the aralkyloxy include benzyl, phenethyl and the like. Examples of the aroyl moiety in the aroyl and the aroyloxy include benzoyl, naphthoyl and the like. Examples of the arylalkyl moiety of the arylalkanoyloxy are benzyl, phenethyl and the like. Examples of the substituent(s) in the substituted lower alkoxy include hydroxy, lower alkoxy, halogen, amino, azido, carboxy, lower alkoxycarbonyl and the like. Herein, the lower alkyl moiety of the lower alkoxy and the lower alkoxycarbonyl has the same meaning as the above-described lower alkyl, and the halogen has the same meaning as described above.

Hereinafter, a compound represented by formula (I) will be referred to as Compound (I).

Examples of the pharmaceutically acceptable salt of Compound (I) are pharmaceutically acceptable acid addition salt, metal salt, ammonium salt, organic amine addition salt, amino acid addition salt and the like.

Examples of the pharmaceutically acceptable acid addition salts of Compound (I) include an inorganic acid salt such as hydrochloride, sulfate and phosphate; and an organic acid salt such as acetate, maleate, fumarate, tartrate, citrate and methanesulfonate. Examples of the pharmaceutically acceptable metal salts include an alkali metal salt such as sodium salt and potassium salt; alkaline earth metal salt such as magnesium salt and calcium salt; aluminum salt; zinc salt and the like. Examples of the pharmaceutically acceptable ammonium salts include ammonium, tetramethylammonium and the like. Examples of the pharmaceutically acceptable organic amine addition salt include an addition salt of morpholine, piperidine and the like. Examples of the pharmaceutically acceptable amino acid addition salts include an addition salt of lysine, glycine, phenylalanine and the like.

Compound (I) is able to be produced by a process disclosed in Japanese Published Examined Patent Application No. 26,516/1972; Journal of Medicinal Chemistry (J. Med. Chem.), vol. 34, p. 1431 (1991); Journal of Medicinal Chemistry (J. Med. Chem.), vol. 36, p. 1333 (1993); WO 92/06976; Japanese Published Unexamined Patent Application No. 211, 856/1994; Japanese Published Unexamined Patent Application No. 239,862/1994; WO 95/23165; Japanese Published Unexamined Patent Application No. 16559/1994; WO 94/01114; WO 99/12546; WO 99/35147 and the like, or by a process similar thereto. The desired compound in each production process can be isolated and purified by a purifying method which has been commonly used in synthetic organic chemistry such as filtration, extraction, washing, drying, concentration, recrystallization and various chromatographies.

When it is desired to obtain a salt of Compound (I), in the case where Compound (I) is produced in the form of the salt, it can be purified as it is, but where it is produced in its free form, it can be converted into a salt, after being dissolved or suspended in an appropriate solvent followed by adding an appropriate acid or base.

Furthermore, Compound (I) and pharmaceutically acceptable salts thereof may exist in the form of adducts with water or various solvents, and these adducts are also used as the agents for treating migraine of the present invention.

For some of Compounds (I), there may exist optical isomers and the like, but all possible isomers including them and mixtures thereof may be used as the agents for treating migraine of the present invention.

Specific examples of Compound (I) are shown in Table 1.

TABLE 1

| Compound No. | Structure |
|---|---|
| 1 | $H_3C$-N, $CH_3$-N, with 3,4,5-tri-$OCH_3$ styryl xanthine |
| 2 | $CH_3CH_2$-N, $CH_3$-N, $CH_2CH_3$, with 3,4-di-$OCH_3$ styryl xanthine |
| 3 | $CH_3(CH_2)_2$-N, $CH_3$-N, $(CH_2)_2CH_3$, with 3,4-di-$OCH_3$ styryl xanthine |
| 4 | $CH_3CH_2$-N, $CH_3$-N, $CH_2CH_3$, with methylenedioxy-$OCH_3$ styryl xanthine |

The effect of the present invention will be explained by the following Test Examples.

TEST EXAMPLE 1

Contractile Effects on Basilar Arteries

Dogs were anesthetized by intravenous injection of sodium pentobarbital, after which they were euthanized by exsanguination and subjected to craniotomy.

The basilar (cerebral) arteries were removed and cut into rings segments of about 2 mm in width. Each ring segment was fixed with a silk thread to a needle cut into about 2 mm in length. The needle was attached to a holder provided in an Easy-Magnus System (Model no. UC-2; IWASHIYA KISHIMOTO MEDICAL INSTRUMENTS); the ring segments were immersed in a nutritive solution and allowed to stabilize at a resting tension of 0.2 g (1.96 mN) for more than 60 minutes. Into the organ bath (2 mL) of the Easy-Magnus System, the cerebral artery was relaxed by application of 2 μL of 10 mmol/L adenosine aqueous solution. After that, the test compound was added cumulatively; 1 μL of 0.2 mmol/L dimethylsulfoxide solution, 1 μL of 0.4 mmol/L dimethylsulfoxide solution, and 0.7 μL of 2 mmol/L dimethylsulfoxide solution in order (Test compound-added group). Separately, in the same manner as in the Test compound-added group, dimethylsulfoxide alone was cumulatively added in place of the test compound (Vehicle group). The contraction of the cerebral artery was recorded on a recorder (Yokogawa) from an isometric force transducer (Nihon Kohden) connected to the holder, to which the ring was fixed, through a strain-pressure amplifier (Nihon Kohden).

The contractile effects were shown in FIG. 1 as a suppressive rate (%) of the test compound to the adenosine-induced relaxation of the cerebrovascular smooth muscle.

From the above results, the followings became clear.

The relaxation was recognized with addition of adenosine in the isolated cerebral artery, and the adenosine-induced relaxation of the cerebral artery was dose-dependently and significantly suppressed by addition of Compound 2, in comparison with the Vehicle group.

From the above results of Test Example 1, it was found that Compound (I) or a pharmaceutically acceptable salt thereof suppress the dilation of the cerebral vessel and contracting the cerebral vessel. In other words, it was suggested that Compounds (I) or a pharmaceutically acceptable salt thereof is useful as a therapeutic agent for migraine.

Compound (I) or a pharmaceutically acceptable salt thereof may be used either as it is or in various pharmaceutical dosage forms. The pharmaceutical composition of the present invention may be manufactured by a uniform mixing of Compound (I) or a pharmaceutically acceptable salt thereof as an active ingredient in an effective dose with a pharmaceutically acceptable carrier. It is preferred that such a pharmaceutical composition is in a unit dosage form suitable for the administration such as rectal administration or oral or parenteral administration (including subcutaneous, intravenous and intramuscular).

In preparing a composition in an orally administering form, any useful pharmaceutically acceptable carrier may be used. In the case of oral liquid preparation such as suspension and syrup, it may be manufactured using water, saccharide such as sucrose, sorbitol and fructose, glycol such as polyethylene glycol and propylene glycol, oil such as sesame oil, olive oil and soybean oil, antiseptic agent such as p-hydroxybenzoate, flavor such as strawberry flavor and peppermint, etc. In the case of diluted powder, pill, capsule and tablet, it may be prepared using excipient such as lactose, glucose, sucrose and mannitol, disintegrating agent such as starch and sodium alginate, lubricant such as magnesium stearate and talc, binder such as polyvinyl alcohol, hydroxypropyl cellulose and gelatin, surfactant such as fatty acid ester, plasticizer such as glyceline, and the like. Tablets and capsules are the most useful unit agents being administered per os because their administration is easy. In the manufacture of tablets and capsules, a solid pharmaceutical carrier is used.

Injection preparation can be prepared using a carrier comprising distilled water, salt solution, glucose solution or a mixture of brine and glucose solution, or the like. In that case, it is prepared as solution, suspension or dispersion using an appropriate adjuvant according to the conventional method.

Compound (I) or a pharmaceutically acceptable salt thereof can be administered orally in the above-described pharmaceutical dosage form or parenterally as injections. Although effective dose and administering frequency thereof vary depending upon administration form, age and body weight of a patient, symptom, etc., it is appropriate to administer 1 to 100 mg/60 kg/day or, preferably, 1 to 20 mg/60 kg/day once daily or several times a day.

-○-: Vehicle group

-●-: Compound 2-added group

Figure 1:
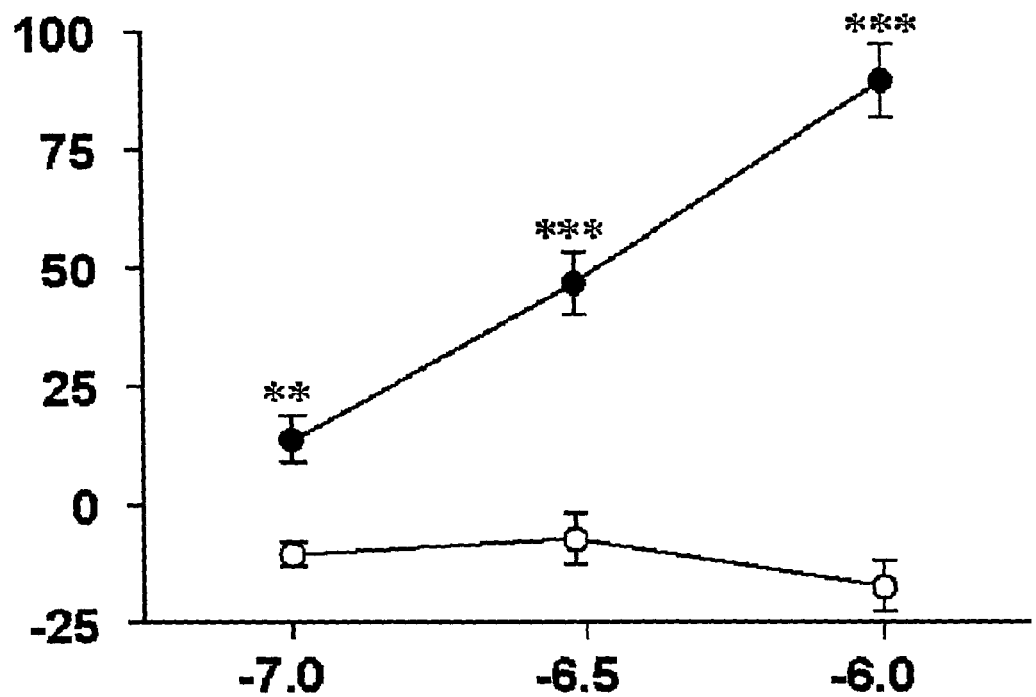
FIG. 1 shows a suppressive effect of Compound 2 on the adenosine-induced relaxation of the cerebrovascular smooth muscle. The ordinate indicates the suppressive rate (%) of the adenosine-induced relaxation of the cerebrovascular smooth muscle, and the abscissa indicates the logarithm (log [mol/L]) of concentration of Compound 2 added. Each plot on the graph means the followings.

**: indicating the significant difference of $p<0.01$ (Student's t-test)

***: indicating the significant difference of $p<0.001$ (Student's t-test)

BEST MODE FOR CARRYING OUT THE INVENTION

Embodiments of the present invention are illustrated in detail below referring to examples.

Example 1

Tablets

Tablets comprising the following composition are prepared by a conventional method.

Compound 1 (40 g), 286.8 g of lactose and 60 g of potato starch are mixed and 120 g of a 10% aqueous solution of hydroxypropyl cellulose is added thereto. The mixture is kneaded by a conventional method, granulated, dried and subjected to particle size selection to give granules for tablets. Magnesium stearate (1.2 g) is added thereto and mixed therewith and subjected to tabletting using a tabletting machine (RT-15 manufactured by Kikusuisha) having punches with 8 mm diameter to give tablets (each tablet containing 20 mg of the active ingredient).

| Prescription | |
|---|---|
| Compound 1 | 20 mg |
| Lactose | 143.4 mg |
| Potato starch | 30 mg |
| Hydroxypropyl cellulose | 6 mg |
| Magnesium stearate | 0.6 mg |
| | 200 mg |

Example 2

Capsule Preparations

Capsule preparations comprising the following composition are prepared by a conventional method.

Compound 2 (200 g), 995 g of Avicel and 5 g of magnesium stearate are mixed by a conventional method. The mixture is filled in hard capsules No. 4 (capacity of one capsule is 120 mg) using a capsule filling machine (type LZ-64; manufactured by Zanasi) to prepare capsule preparations (each capsule containing 20 mg of the active ingredient).

| Prescription | |
|---|---|
| Compound 2 | 20 mg |
| Avicel | 99.5 mg |
| Magnesium stearate | 0.5 mg |
| | 120 mg |

Example 3

Injection Preparations

Injection preparations comprising the following composition are prepared by a conventional method.

Compound 3 (1 g) is dissolved in 100 g of pure soybean oil and 12 g of pure yolk lecithin and 25 g of glycerol for injection are added thereto. The mixture is made 1,000 mL using distilled water for injection by a conventional method followed by kneading and emulsifying. The resulting dispersion is subjected to an aseptic filtration using a membrane filter of a disposable type of 0.2 μm and each 2 mL thereof is aseptically filled in a glass vial to prepare injection preparations (each vial containing 2 mg of the active ingredient).

| Prescription | |
|---|---|
| Compound 3 | 2 mg |
| Pure soybean oil | 200 mg |
| Pure yolk lecithin | 24 mg |

-continued

| Prescription | |
|---|---|
| Glycerol for injection | 50 mg |
| Distilled water for injection | 1.72 mL |
| | 2.00 mL |

INDUSTRIAL APPLICABILITY

The present invention provides agents for treating migraine comprising, as an active ingredient, for example, a xanthine derivative or a pharmaceutically acceptable salt thereof.

The invention claimed is:

1. A method for treating migraine which comprises administering to a patient in need thereof an effective amount of a compound represented by formula (2)

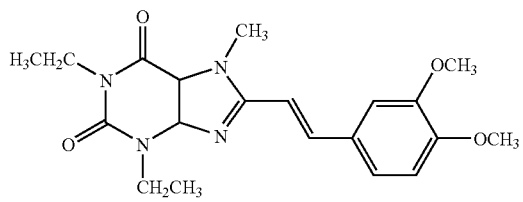

(2)

or a pharmaceutically acceptable salt thereof.

* * * * *